United States Patent
Biadatti-Portal

(10) Patent No.: US 8,163,952 B2
(45) Date of Patent: Apr. 24, 2012

(54) RAR RECEPTOR AGONIST LIGANDS AND USE THEREOF IN HUMAN MEDICINE AND COSMETICS

(75) Inventor: Thibaud Biadatti-Portal, Opio (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 12/599,624

(22) PCT Filed: Apr. 24, 2008

(86) PCT No.: PCT/FR2008/050747
§ 371 (c)(1),
(2), (4) Date: Jun. 30, 2010

(87) PCT Pub. No.: WO2008/152260
PCT Pub. Date: Dec. 18, 2008

(65) Prior Publication Data
US 2010/0261754 A1    Oct. 14, 2010

(30) Foreign Application Priority Data
May 11, 2007    (FR) ...................................... 07 55019

(51) Int. Cl.
   *C07C 229/00*    (2006.01)
(52) U.S. Cl. ......................................... 560/45
(58) Field of Classification Search .................. None
   See application file for complete search history.

(56) References Cited

U.S. PATENT DOCUMENTS
7,326,803 B2   2/2008 Biadatti et al.
2005/0131033 A1*   6/2005 Biadatti et al. ............. 514/355

FOREIGN PATENT DOCUMENTS
FR    2 840 300    12/2003
WO    WO 03/101928 A1    12/2003

OTHER PUBLICATIONS
Silverman (The Organic Chemistry of Drug Design and Drug Action, 1992, Academic Press Inc.).*
English language abstract of FR 2 840 300 (2003).
International Search Report for PCT/FR2008/050747, dated Dec. 10, 2008.

* cited by examiner

*Primary Examiner* — Daniel Sullivan
*Assistant Examiner* — Jennifer C Sawyer
(74) *Attorney, Agent, or Firm* — Finnegan, Henderson, Farabow, Garrett & Dunner, LLP

(57) ABSTRACT

The invention relates to compounds corresponding to general formula (I) below:

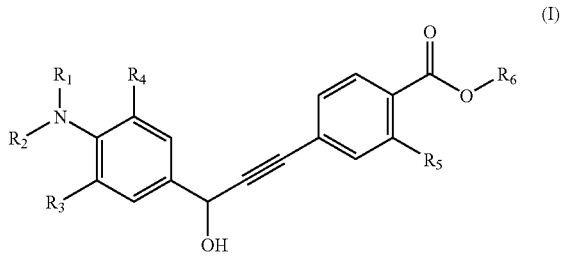

to the compositions containing same, to methods for the preparation thereof and to the use thereof in pharmaceutical compositions for use in human or veterinary medicine, or else in cosmetic compositions.

16 Claims, 1 Drawing Sheet

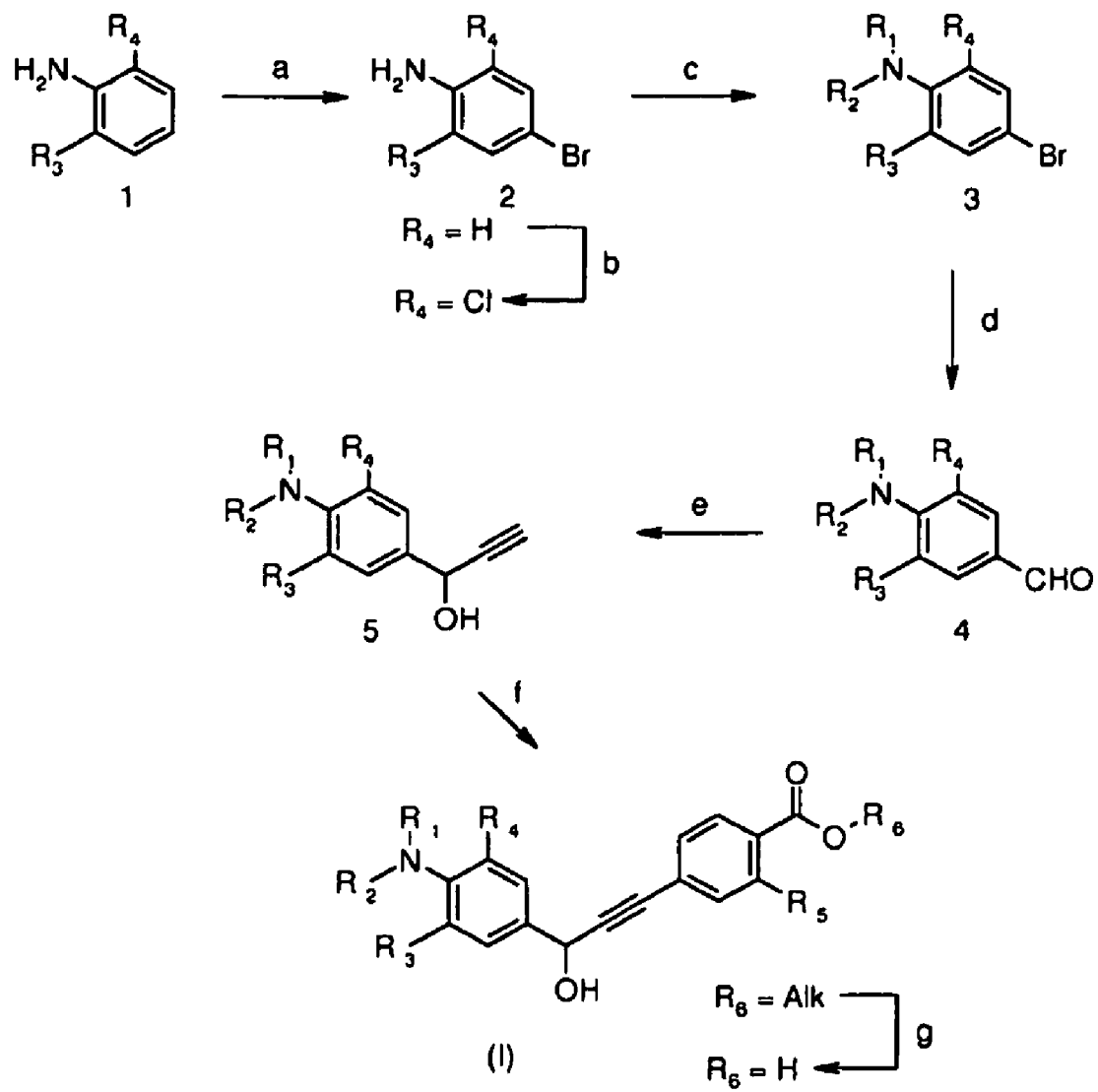

RAR RECEPTOR AGONIST LIGANDS AND USE THEREOF IN HUMAN MEDICINE AND COSMETICS

This application is a national stage entry of International Application No. PCT/FR2008/050747, filed on Apr. 24, 2008, which claims priority to French Application No. FR 0755019, filed May 11, 2007.

The invention relates to novel compounds, which are RAR receptor agonist ligands, as novel and useful industrial products. It also relates to compositions containing same, to methods for the preparation thereof and to the use thereof in pharmaceutical compositions for use in human or veterinary medicine, or else in cosmetic compositions, and to the non-therapeutic use of the latter.

Compounds with activity of retinoid type (vitamin A and derivatives thereof) are widely described in the literature as having activities in cell proliferation and differentiation processes. These properties give this class of compounds a high potential in the treatment or prevention of numerous pathological conditions, and more particularly in dermatology and cancer. Most of the biological effects of retinoids are mediated by modulating the nuclear retinoic acid receptors (RARs).

RAR receptors activate transcription by binding to DNA sequence elements, known as RAR response elements (RARE), in the form of a heterodimer with retinoid X receptors (known as RXRs).

Three subtypes of human RARs have been identified and described: RARα, RARβ and RARγ.

The prior art contains a large number of chemical compounds that are ligands of RAR-type receptors. Among the prior art documents, mention may, for example, be made of patent EP 0 816 352 B1 which describes aromatic biaryl heterocyclic compounds for the treatment of dermatological, rheumatic, respiratory and opthalmological conditions, but also for cosmetic uses, document WO 2005/056510 which describes molecules comprising an aromatic ring substituted with a hydroxyalkyl radical, documents WO 99/10308 and WO 2006/066978 which describe substituted biphenyl derivatives, documents U.S. Pat. No. 6,218,128 and EP 0879814 which describe bicyclic and/or tricyclic compounds, document EP 0850909 which describes stilbene compounds, document WO 98/56783 which describes biaromatic compounds, and documents EP 0776885 and EP 0776881 which describe biaromatic compounds comprising adamantyl groups.

The gamma subtype of the RAR receptor family is largely predominant in the epidermis, where it represents approximately 90% of the total receptors ("Retinoic acid receptors and binding proteins in human skin", Elder J T, Astrom A, Pettersson U, Tavakkol A, Krust A, Kastner P, Chambon P, Voorhees J J: *J Invest Dermatol*. 1992; 98 (6 suppl): 36S-41S; or: "Retinoic acid receptor expression in human skin keratinocytes and dermal fibroblasts in vitro", Redfern C P, Todd C. *J Cell Sci*. 1992; 102 (Pt 1): 113-21) and it is indeed the interaction with this RAR gamma receptor which is responsible for the effectiveness of retinoids on the epidermis ("Retinoic acid receptor gamma mediates topical retinoid efficacy and irritation in animal models", Chen S, Ostrowski J, Whiting G, Roalsvig T, Hammer L, Currier S J, Honeyman J, Kwasniewski B, Yu K L, Sterzycki R, et al. *J Invest Dermatol*. 1995; 104 (5): 779-83).

RAR gamma receptors are therefore the only target in the treatment of pathological conditions at the level of the epidermis, for instance for acne or psoriasis or any other pathological skin conditions treated with retinoids.

Now, the Applicant has synthesized novel compounds that are RARγ-selective agonists.

Thus, the present invention relates to compounds of general formula (I) below:

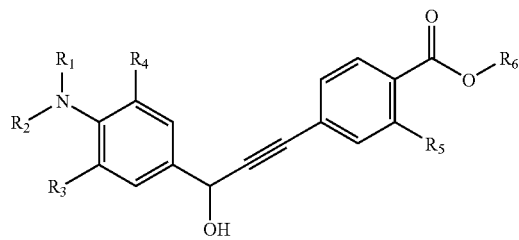

in which:
- $R_1$ is a hydrogen atom, or an alkyl radical containing from 1 to 4 carbon atoms,
- $R_2$ is an alkyl radical containing from 1 to 4 carbon atoms, or else $R_1$ and $R_2$ form, together with the nitrogen atom N to which they are attached, a heterocycle of piperidine or pyrrolidine type,
- $R_3$ is an alkyl radical containing from 1 to 4 carbon atoms,
- $R_4$ is a hydrogen, an alkyl radical containing from 1 to 4 carbon atoms, or a halogen atom,
- $R_5$ is a hydrogen atom or a hydroxyl,
- $R_6$ is a hydrogen atom, or an alkyl radical containing from 1 to 4 carbon atoms, and the salts of the compounds of formula (I), in particular when $R_6$ represents a hydrogen atom, and also the optical isomers of said compounds of formula (I).

According to the present invention, the expression "alkyl radical containing from 1 to 4 carbon atoms" denotes a linear or branched, saturated hydrocarbon-based chain containing from 1 to 4 carbon atoms.

Preferably, such a radical is chosen from methyl, ethyl, propyl, butyl, 2-methylpropyl, i-propyl and t-butyl radicals.

The term "halogen" is intended to mean preferably a chlorine, bromine, fluorine or iodine atom.

When the compounds according to the invention are in the form of salts of the carboxylic acid function ($R_6$=H), the salt is preferably a salt of an alkali metal or alkaline-earth metal, or else a zinc salt or a salt of an organic amine.

When the compounds according to the invention have an amine function (i.e. when $R_1$ is a hydrogen atom or an alkyl radical containing from 1 to 4 carbon atoms, and $R_2$ is an alkyl radical containing from 1 to 4 carbon atoms) and are in the form of salts of this amine, they are salts of an inorganic acid, for instance hydrochloric acid, sulphuric acid or hydrobromic acid, or salts of an organic acid, for instance acetic acid, triflic acid, tartaric acid, oxalic acid, citric acid or trifluoroacetic acid.

According to the present invention and in one advantageous embodiment, the compounds of the invention are those from which at least one and preferably all of the conditions below are met:
- $R_1$ is chosen from a hydrogen atom or a methyl or ethyl radical,
- $R_2$ is chosen from a methyl, ethyl and a 2-methylpropyl radical or
- $R_1$ and $R_2$ form, together with the nitrogen atom N to which they are attached, a heterocycle of piperidine or pyrrolidine type,
- $R_3$ is chosen from i-propyl and t-butyl radicals, $R_4$ is chosen from a hydrogen atom, a methyl or ethyl radical, an i-propyl radical and a chlorine atom, $R_5$ is a hydrogen atom or a hydroxyl, $R_6$ is a hydrogen atom or an alkyl radical containing from 1 to 4 carbon atoms.

Among the compounds of formula (I) which fall within the context of the present invention, mention may in particular be made of the following compounds:

1/—4-[(tert-butyldiethylaminophenyl)hydroxyprop-1-ynyl]benzoic acid

2/—4-{[tert-butyl(ethylisobutylamino)phenyl]hydroxyprop-1-ynyl}benzoic acid

3/—4-[3-(3-tert-butyl-4-dimethylaminophenyl)-3-hydroxyprop-1-ynyl]benzoic acid

4/—4-[3-(3-tert-butyl-4-pyrrolidin-1-ylphenyl)-3-hydroxyprop-1-ynyl]benzoic acid 5/—4-[3-(3-tert-butyl-4-piperidin-1-ylphenyl)-3-hydroxyprop-1-ynyl]benzoic acid 6/—4-[3-(3-tert-butyl-4-diethylaminophenyl)-3-hydroxyprop-1-ynyl]-2-hydroxybenzoic acid 7/—4-[3-(3-tert-butyl-5-chloro-4-dimethylaminophenyl)-3-hydroxyprop-1-ynyl]benzoic acid 8/—4-[3-(3-tert-butyl-5-chloro-4-dimethylaminophenyl)-3-hydroxyprop-1-ynyl]-2-hydroxybenzoic acid 9/—4-[3-(4-dimethylamino-3,5-diisopropylphenyl)-3-hydroxyprop-1-ynyl]benzoic acid 10/—4-[3-(4-dimethylamino-3,5-diisopropylphenyl)-3-hydroxyprop-1-ynyl]-2-hydroxybenzoic acid 11/—4-[3-(4-diethylamino-3-isopropylphenyl)-3-hydroxyprop-1-ynyl]benzoic acid 12/—(−)-4-[3-(3-tert-butyl-4-diethylaminophenyl)-3-hydroxyprop-1-ynyl]benzoic acid 13/—(+)-4-[3-(3-tert-butyl-4-diethylaminophenyl)-3-hydroxyprop-1-ynyl]benzoic acid.

A subject of the present invention is also the methods for preparing the compounds of formula (I), in particular according to the reaction scheme given in FIG. 1.

The intermediates of general formula 2 can be obtained from the starting products 1 after a first stage of bromination in the para-position, according to methods described, for example, in Sugimoto, A. et al.; *Heterocycl Chem* 1999, 36(4), 1057-1064 or Berthelot, J. et al.; *Synth Commun* 1986, 16, 1641. When $R_4$=Cl, the introduction of the chlorine can be carried out by means of a conventional halogenation reaction, for example in accordance with Silvestri, R. et al.; *Org Prep Proced Int* 2002, 34 (5), 507-510. A sequence of two reactions comprising alkylation of the aniline function in the presence of dialkyl sulphate or of an alkyl halide and of a base (see, for example, Dehmlow, E. V., *Tet Lett* 1985, 25, 97) or in accordance with the methods described, for example, in "Chemistry of the amino group" by S. Patai (Wiley-Interscience, NY 1968) pages 669-682, makes it possible to obtain the compounds of formula 3. In the case where $N(R_1R_2)$ forms a pyrrolidine or piperidine ring, the formation of the ring, for example in the presence of 1,4-dihalobutane or 1,5-dihalopentane and of a base, or by means of a method described in "Chemistry of the amino group" by S. Patai (Wiley-Interscience, NY 1968) pages 669-682, makes it possible to obtain the corresponding compounds 3. Alternatively, these same compounds of general formula 3 can be generated after para-bromination, and then formation and reduction of a pyrrolidinone or succinimide group or a piperidone group (see, for example, Ohta, S. *Heterocycles* 1993, 36 (4), 743; Hubbard, J. L.; *J Heterocycl Chem* 1992, 29 (4), 719; Akula, M. R.; *Synth Commun* 1998, 28 (11), 2063; Collins, C. J. *Tetrahedron Lett* 1999, 40 (19), 3673). The introduction of the aldehyde function is obtained by reaction of an organolithium compound or an organomagnesium compound derived from 3 and reaction thereof on an appropriate electrophile such as DMF (see, for example, Worden, L. R. at al.; *J Chem Soc C* 1970, 227 or Vuligonda, V. et al.; *Bioorg Med Chem Lett* 1999, 9 (5), 743-748). The addition of an organometallic alkynide, for instance ethynylmagnesium bromide (see, for example, Gray, M. et al.; *Synlett* 1992, (7), 597-598), enables the synthesis of the intermediates of general formula 5. The compounds of general formula (I) can in this case be obtained by Sonogashira coupling of these compounds 5 with corresponding halogenated aryl derivatives, for instance 4-iodobenzoic acid or 4-iodosalicylic acid, or the corresponding esters in the presence of palladium catalysts. As precedents in the literature, mention may, for example, be made of patent EP 661258 or else the publication by Sonogashira, K. et al.; *Tetrahedron Lett* 1975 (50), 4467. Finally, in the case where $R_6$=H and when the coupling described above is carried out with an ester partner instead of the carboxylic acid partner, the advanced intermediates (I) where $R_6$ represents an alkyl radical containing from 1 to 4 carbon atoms can be subjected to reactions for saponification or for hydrolysis of the ester function so as to give a carboxylic acid function, for example using conditions among those described in "Comprehensive organic transformations" by R. C. Larock, 2nd edition (J. Wiley & Sons), pages 1959-1968.

The compounds according to the invention have retinoic acid receptor (RAR) agonist properties. This activity on RARα, β and γ receptors is measured in a transactivation test and quantified by means of the dissociation constant Kdapp (apparent).

The preferred compounds of the present invention have a dissociation constant of less than or equal to 5000 nM, and advantageously less than or equal to 1000 nM, and preferentially less than or equal to 100 nM on the RARγ subtype, with a selectivity versus RARα and RARβ of greater than or equal to a factor of 2, and preferentially to a factor of 10.

A subject of the present invention is also the compounds of formula (I) as described above, as a medicament.

The compounds according to the invention are particularly suitable in the following treatment fields:

1/ for treating dermatological conditions associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;

2/ for treating other types of keratinization disorders, in particular ichthyosis, ichthyosiform conditions, Darier's disease, palmoplantar keratoderma, leukoplakia and leucoplakiform conditions, and cutaneous or mucosal (oral) lichen;

3/ for treating other dermatological conditions with an inflammatory immunoallergic component, with or without a cell proliferation disorder, and in particular all forms of psoriasis, whether cutaneous, mucosal or ungual, and even psoriatic arthritis, or else cutaneous atopy, such as eczema, or respiratory atopy or else gingival hypertrophy;

4/ in the treatment of skin disorders due to exposure to UV radiation, and also for repairing or combatting aging of the skin, whether photoinduced or chronological, or for reducing actinic pigmentations and keratosis, or any pathological conditions associated with chronological or actinic aging, such as xerosis;

5/ for treating all dermal or epidermal proliferations, whether they are benign or malignant, whether or not they are of viral origin, such as common warts, flat warts or epidermodysplasia vurruciformis, oral or florid papillomatoses, T lymphoma, and proliferations that may be induced by ultraviolet radiation, in particular in the case of basocellular and spinocellular epithelioma, and also any precancerous skin lesion such as keratoacanthomas;

6/ for treating other dermatological disorders such as immune dermatoses, for instance lupus erythematosus, bullous immune diseases and collagen diseases, such as scleroderma;

7/ in the treatment of dermatological or systemic conditions with immunological components;

8/ for treating certain opthalmological disorders, in particular corneopathies;

9/ for preventing or curing the stigmata of epidermal and/or dermal atrophy induced by local or systemic corticosteroids, or any other form of cutaneous atrophy;

10/ in the treatment of any cutaneous or systemic complaint of viral origin;

11/ for combatting sebaceous function disorders, such as hyperseborrhoea of acne or simple seborrhoea;

12/ for preventing or treating cicatrization disorders, or for preventing or repairing stretch marks, or else for promoting cicatrization;

13/ in the treatment of pigmentation disorders, such as hyperpigmentation, melasma, hypopigmentation or vitiligo;

14/ in the treatment of lipid metabolism conditions, such as obesity, hyperlipidemia or non-insulin-dependent diabetes;

15/ in the treatment of inflammatory conditions such as arthritis;

16/ in the treatment or prevention of cancerous or precancerous conditions;

17/ in the prevention or treatment of alopecia of various origins, in particular alopecia caused by chemotherapy or by radiation;

18/ in the treatment of immune system disorders, such as asthma, type I sugar diabetes, multiple sclerosis, or other selective dysfunctions of the immune system; and 19/ in the treatment of cardiovascular system conditions, such as arteriosclerosis or hypertension.

A subject of the present invention is also a pharmaceutical composition comprising, in a physiologically acceptable medium, at least one compound of formula (I) as defined above.

A subject of the present invention is also a novel medicinal composition for use in particular in the treatment of the abovementioned conditions, and which is characterized in that it comprises, in a pharmaceutically acceptable medium that is compatible with the method of administration selected for this composition, at least one compound of formula (I), an optical isomer thereof or a salt thereof.

The composition according to the invention may be administered orally, enterally, parenterally, topically or ocularly. Preferably, the pharmaceutical composition is packaged in a form that is suitable for topical application. The term "topical application" is intended to mean application to the skin or the mucous membranes.

When administered orally, the composition may be in the form of tablets, gel capsules, dragees, syrups, suspensions, solutions, powders, granules, emulsions, suspensions of microspheres or nanospheres or of lipid or polymer vesicles for controlled release. When administered parenterally, the composition may be in the form of solutions or suspensions for a drip or for injection.

The compounds according to the invention are generally administered at a daily dose of approximately 0.01 mg/kg to 100 mg/kg of body weight, in one or more dosage intakes.

The compounds are used systemically at a concentration generally between 0.001% and 10% by weight, preferably between 0.01% and 1% by weight, relative to the weight of the composition.

When administered topically, the pharmaceutical composition according to the invention is more particularly for use in treating the skin and the mucous membranes and may be in liquid, pasty or solid form, and more particularly salves, creams, milks, ointments, powders, impregnated pads, syndets, solutions, gels, sprays, foams, suspensions, sticks, shampoos or washing bases. It may also be in the form of suspensions of microspheres or nanospheres or of lipid or polymer vesicles or gelled or polymer patches for controlled release.

The compounds are used topically at a concentration generally of between 0.001% and 10% by weight, preferably between 0.01% and 1% by weight, relative to the total weight of the composition.

The compounds of formula (I) according to the invention also find a use in the cosmetics fields, in particular in body and hair hygiene and especially for treating acne-prone skin, for promoting hair regrowth or for limiting hair loss, for combatting the greasy appearance of the skin or the hair, in protection against the harmful aspects of sunlight or in the treatment of physiologically dry skin, and for preventing and/or combatting photoinduced or chronological aging.

A subject of the invention is thus also a cosmetic composition comprising, in a physiologically acceptable medium, at least one compound of formula (I).

A subject of the invention is also the nontherapeutic use of a cosmetic composition comprising at least one compound of formula (I), for preventing and/or treating the signs of skin aging and/or dry skin.

A subject of the invention is also the nontherapeutic use of a cosmetic composition comprising at least one compound of formula (I), for body or hair hygiene.

The cosmetic composition according to the invention containing, in a physiologically acceptable medium, at least one compound of formula (I) or an optical or geometrical isomer thereof or a salt thereof, may be in particular in the form of a cream, a milk, a gel, suspensions of microspheres of nanospheres or lipid or polymer vesicles, impregnated pads, solutions, sprays, foams, sticks, soaps, washing bases or shampoos.

The concentration of compound of formula (I) in the cosmetic composition is preferably between 0.001% and 3% by weight, relative to the total weight of the composition.

The term "physiologically acceptable medium" is intended to mean a medium that is compatible with the skin and, optionally, with the skin appendages (eyelashes, nails, hair) and/or the mucous membranes.

The pharmaceutical and cosmetic compositions as described above may also contain inert additives, or even pharmacodynamically active additives as regards the pharmaceutical compositions, or combinations of these additives, and in particular:

wetting agents;
flavour enhancers;
preservatives such as para-hydroxybenzoic acid esters;
stabilizers;
moisture regulators;
pH regulators;
osmotic pressure modifiers;
emulsifiers;
UV-A and UV-B screening agents;

antioxidants, such as α-tocopherol, butylhydroxy-anisole or butylhydroxytoluene, superoxide dismutase, ubiquinol or certain metal-chelating agents;

depigmenting agents such as hydroquinone, azelaic acid, cafeic acid or kojic acid;

emollients;

moisturizers, for instance glycerol, PEG 400, thiamorpholinone and its derivatives or urea;

antiseborrhoeic or anti-acne agents, such as S-carboxymethylcysteine, S-benzylcysteamine, salts thereof or derivatives thereof, or benzoyl peroxide;

antibiotics such as erythromycin and its esters, neomycin, clindamycin and its esters, and tetracyclines;

antifungal agents such as ketoconazole or poly-4,5-methylene-3-isothiazolidones;

agents for promoting hair regrowth, such as minoxidil (2,4-diamino-6-piperidinopyrimidine 3-oxide) and its derivatives, diazoxide (7-chloro-3-methyl-1,2,4-benzothiadiazine 1,1-dioxide) and phenyloin (5,4-diphenylimidazolidine-2,4-dione);

nonsteroidal anti-inflammatories;

carotenoids, and in particular β-carotene;

anti-psoriatic agents such as anthralin and its derivatives;

eicosa-5,8,11,14-tetraynoic acid and eicosa-5,8,11-triynoic acid, and esters and amides thereof;

retinoids, i.e. natural or synthetic RXR receptor ligands;

corticosteroids or oestrogens;

α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicyclic acid and its salts, amides or esters;

ion-channel blockers such as potassium-channel blockers;

or alternatively, more particularly for the pharmaceutical compositions, in combination with medicaments known to interfere with the immune system (for example, cyclosporin, FK 506, glucocorticoids, monoclonal antibodies, cytokines or growth factors, etc.).

Of course, those skilled in the art will take care to select the optional compound(s) to be added to these compositions in such a way that the advantageous properties intrinsically associated with the present invention are not, or are not substantially, impaired by the envisaged addition.

Another subject of the invention relates to a cosmetic method for enhancing the appearance of the skin, characterized in that a composition comprising at least one compound of formula (I) as defined above is applied to the skin.

Activation of the retinoic acid receptors by the compounds of formula (I) according to the invention makes it possible to obtain skin that has an enhanced surface appearance.

Several examples of the production of active compounds of formula (I) according to the invention, biological activity results and also various concrete formulations based on such compounds will now be given by way of illustration and with no limiting nature.

EXAMPLE 1

4-[(tert-butyldiethylaminophenyl)hydroxy-prop-1-ynyl]benzoic acid a/ 4-Bromo-2-tert-butylphenylamine 25 g (168 mmol) of 2-tert-butylaniline are placed in 300 ml of acetic acid. 450 ml of aqueous HBr at 48% are added and the mixture is then cooled to 0° C. 150 ml of DMSO are added dropwise, the mixture having been brought back to ambient temperature is stirred for 2 hours and it is then poured into ice-cold water and basified to pH 10 with 5N NaOH. It is extracted with diethyl ether and the organic phase is then dried and concentrated to dryness. The residue is column-purified (95/5 heptane/EtOAc). 25.2 g of 4-bromo-2-tert-butylphenylamine are obtained in the form of a yellow oil (yield=65%).

b/ (4-Bromo-2-tert-butylphenyl)ethylamine 2.7 g (68 mmol) of sodium hydride are suspended in 250 ml of DMSO, under a stream of nitrogen. 7 g (31 mmol) of 4-bromo-2-tert-butylphenylamine, diluted in 10 ml of DMSO, are added to the reaction medium cooled to 0° C. After stirring at ambient temperature for 30 minutes, 5.4 ml (68 mmol) of ethyl iodide are added slowly. The pale-yellow-coloured mixture is stirred overnight at ambient temperature and then poured into a saturated solution of ammonium chloride and extracted twice with ethyl acetate. The organic phase is dried and then concentrated under vacuum. 5 g of (4-bromo-2-tert-butylphenyl)ethylamine are obtained in the form of a yellow oil (yield=65%).

c/ (4-Bromo-2-tert-butylphenyl)diethylamine 5 g (20 mmol) of (4-bromo-2-tert-butylphenyl)-ethylamine are dissolved, under a stream of nitrogen, in 200 ml of DMSO. After cooling to 0° C., 1.7 g (43 mmol) of sodium hydride are added slowly. After 30 minutes, 3.4 ml (43 mmol) of iodoethane are added and the mixture is then brought back to ambient temperature and stirred for an entire weekend. It is then poured into a saturated solution of ammonium chloride and extracted twice with diethyl ether. The organic phase is washed with water and then dried and concentrated to dryness. The residue is purified by flash chromatography (95/5 heptane/EtOAc). 3.6 g of (4-bromo-2-tert-butylphenyl)diethylamine are obtained in the form of a yellow oil (yield=63%).

d/ 3-tert-Butyl-4-diethylaminobenzaldehyde 3.6 g (13 mmol) of (4-bromo-2-tert-butylphenyl)-diethylamine are diluted in 100 ml of THF, under a stream of nitrogen. The medium is cooled to −78° C. and then 7.8 ml (20 mmol) of a 2.5M solution of nBuLi are added. After stirring for 45 minutes, 1.5 ml (20 mmol) of DMF are added and the solution is brought back to ambient temperature. After 15 minutes, the mixture is poured into a saturated solution of ammonium chloride and then extracted twice with ethyl acetate. The organic phase is dried over sodium sulphate and then concentrated to dryness. 3.1 g of 3-tert-butyl-4-diethylaminobenzaldehyde are obtained in the form of a yellow oil (yield=100%).

e/ 1-(3-tert-Butyl-4-diethylaminophenyl)prop-2-yn-1-ol 1.5 g (6.7 mmol) of 3-tert-butyl-4-diethylamino-benzaldehyde are dissolved in 20 ml of dry THF, under a light nitrogen flow, at 0° C. 17 ml (8.7 mmol) of a 0.5M solution of ethynylmagnesium bromide are added dropwise and the medium is then brought back to ambient temperature and stirred for 30 minutes. The mixture is then poured into a saturated solution of ammonium chloride, extracted with ethyl acetate, dried over sodium sulphate and then concentrated to dryness. The residue is purified by flash chromatography (90/10 heptane/ ethyl acetate). 780 mg of 1-(3-tert-butyl-4-diethylaminophenyl)prop-2-yn-1-ol are obtained in the form of a colourless oil (yield=47%).

f/ 4-[3-(3-tert-Butyl-4-diethylaminophenyl)-3-hydroxy-prop-1-ynyl]benzoic acid 390 mg of 1-(3-tert-butyl-4-diethylaminophenyl)-prop-2-yn-1-ol (1.6 mmol) and 324 mg (12 mmol) of 4-iodobenzoic acid are diluted in 20 ml of triethylamine and 13 ml of DMF under a light nitrogen flow with 12 mg (0.06 mmol) of copper iodide. After 10 minutes, during which the nitrogen bubbles in the medium, 23 mg (0.03 mmol) of bis(triphenylphosphine)palladium(II) chloride are added. After stirring for 7 hours at ambient temperature, the mixture is poured into a saturated solution of ammonium chloride and then the aqueous phase is brought to pH 5 with 1N HCl. After extraction with ethyl acetate, the organic phase is dried over sodium sulphate and then concentrated to dryness and the residue is purified by silica chromatography (60/40 heptane/ethyl acetate then 80/20 heptane/ethyl acetate).

The 4-[3-(3-tert-butyl-4-diethylaminophenyl)-3-hydroxyprop-1-ynyl]benzoic acid is obtained in the form of a beige solid (m=220 mg, yield=45%, Mp=140° C.)

$^1$H NMR (CDCl$_3$, 400 MHz):

1.00 (t, J=7.2 Hz, 6H); 1.43 (s, 9H); 2.50 (m, 4H); 5.58 (d, J=6 Hz, 1H); 6.13 (d, J=6.4 Hz, 1H); 7.29 (d, J=8 Hz, 1H); 7.37 (d, J=2 Hz, 1H); 7.55 (m, 3H); 7.93 (d, J=8.4 Hz, 2H); 13.2 (m, 1H).

EXAMPLE 2

4-{[tert-butyl(ethylisobutylamino)phenyl]-hydroxyprop-1-ynyl}benzoic acid a/ (4-Bromo-2-tert-butylphenyl)ethylisobutylamine

In a manner analogous to example 1 c, the process is carried out by a reaction of 4 g (16 mmol) of (4-bromo-2-tert-butylphenyl)ethylamine (example 1b) with 1.4 g (34 mmol) of 60% sodium hydride and with 3.7 ml (34 mmol) of 1-bromo-2-methylpropane. 1.5 g of (4-bromo-2-tert-butylphenyl)ethylisobutylamine are obtained in the form of an oil (yield=30%).

b/ 3-tert-Butyl-4-(ethylisobutylamino)benzaldehyde

In a manner analogous to example 1 d, the process is carried out by a reaction of 2 g (5 mmol) of (4-bromo-2-tert-butylphenyl)ethylisobutylamine with 3 ml (7 mmol) of a 2.5M solution of n-butyllithium and 0.6 ml (7 mmol) of DMF. 800 mg of 3-tert-butyl-4-(ethylisobutylamino)benzaldehyde are obtained in the form of a yellow oil (yield=62%).

c/ 1-[3-tert-Butyl-4-(ethylisobutylamino)phenyl]prop-2-yn-1-ol

In a manner analogous to example 1 e, the process is carried out by a reaction of 800 mg (3 mmol) of 3-tert-butyl-4-(ethylisobutylamino)benzaldehyde with 8 ml (4 mmol) of a 0.5M solution of ethynylmagnesium bromide. 700 mg of 1-[3-tert-butyl-4-(ethylisobutyl-amino)phenyl]prop-2-yn-1-ol are obtained in the form of a colourless oil (yield=81%).

d/ 4-{[tert-Butyl(ethylisobutylamino)phenyl]hydroxy-prop-1-ynyl}benzoic acid In a manner analogous to example 1 e, the process is carried out by a reaction of 300 mg (1 mmol) of 1-[3-tert-butyl-4-(ethylisobutylamino)phenyl]prop-2-yn-1-ol with 216 mg (0.87 mmol) of 4-iodobenzoic acid, 12 mg (0.04 mmol) of copper iodide and 15 mg (0.02 mmol) of bis(triphenylphosphine)palladium chloride. 190 mg of 4-{[tert-butyl(ethylisobutylamino)phenyl]hydroxyprop-1-ynyl}benzoic acid are obtained in the form of a beige solid (Mp=117° C., yield=53%).

$^1$H NMR (CDCl$_3$, 400 MHz):

0.86 (m, 9H), 1.44 (s, 9H), 1.99 (m, 2H); 2.50 (m, 1H), 2.80 (m, 3H), 5.59 (d, J=6 Hz, 1H), 6.13 (d, J=6 Hz, 1H), 7.35 (m, 2H), 7.55 (d, J=7.6 Hz, 3H), 7.93 (d, J=8 Hz, 2H), 13.1 (m, 1H).

EXAMPLE 3

4-[3-(3-tert-butyl-4-dimethylaminophenyl)-3-hydroxyprop-1-ynyl]benzoic acid a/ (4-Bromo-2-tert-butylphenyl)methylamine

In a manner analogous to example 1 b, the process is carried out by a reaction of 12 g (53 mmol) of 4-bromo-2-tert-butylphenylamine with 4.7 g (117 mmol) of sodium hydride and 7.2 ml (117 mmol) of methyl iodide. 7.4 g of (4-bromo-2-tert-butylphenyl)methylamine are obtained in the form of a yellow oil (yield=58%).

b/ (4-Bromo-2-tert-butylphenyl)dimethylamine

In a manner analogous to example 1 c, the process is carried out by a reaction of 7.4 g (31 mmol) of (4-bromo-2-tert-butylphenyl)methylamine with 2.7 g (67 mmol) of 60% sodium hydride and with 7.2 ml (67 mmol) of iodomethane. 4.1 g of (4-bromo-2-tert-butylphenyl)dimethylamine are obtained in the form of an oil (yield=52%).

c/ 3-tert-Butyl-4-dimethylaminobenzaldehyde

In a manner analogous to example 1 d, the process is carried out by a reaction of 4.1 g (16 mmol) of (4-bromo-2-tert-butylphenyl)dimethylamine with 9.6 ml (24 mmol) of a 2.5M solution of n-butyllithium and 1.9 ml (24 mmol) of DMF. 2 g of 3-tert-butyl-4-dimethylaminobenzaldehyde are obtained in the form of a yellow oil (yield=100%).

d/ 1-(3-tert-Butyl-4-dimethylaminophenyl)prop-2-yn-1-ol

In a manner analogous to example 1 e, the process is carried out by a reaction of 1 g (4.9 mmol) of 3-tert-butyl-4-dimethylaminobenzaldehyde with 12 ml (6 mmol) of a 0.5M solution of ethynylmagnesium bromide. 900 mg of 1-(3-tert-butyl-4-dimethylaminophenyl)prop-2-yn-1-ol are obtained in the form of a colourless oil (yield=79%).

e/ 4-[3-(3-tert-butyl-4-dimethylaminophenyl)-3-hydroxy-prop-1-ynyl]benzoic acid In a manner analogous to example 1 e, the process is carried out by a reaction of 900 mg (3.8 mmol) of 1-(3-tert-butyl-4-dimethylaminophenyl)prop-2-yn-1-ol with 805 mg (3.2 mmol) of 4-iodobenzoic acid, 30 mg (0.16 mmol) of copper iodide and 56 mg (0.08 mmol) of bis(triphenylphosphine) palladium chloride. 700 mg of 4-[3-(3-tert-butyl-4-dimethylaminophenyl)-3-hydroxyprop-1-ynyl]benzoic acid are obtained in the form of a beige solid (Mp=139° C., yield=64%).

¹H NMR (CDCl₃, 400 MHz):
1.48 (s, 9H), 2.63 (s, 6H), 5.69 (s, 1H), 7.42 (d, J=8 Hz, 1H), 7.50 (m, 1H), 7.58 (s, 1H), 7.60 (m, 2H), 8.08 (d, J=8 Hz, 2H).

EXAMPLE 4

4-[3-(3-tert-butyl-4-pyrrolidin-1-ylphenyl)-3-hydroxyprop-1-ynyl]benzoic acid a/ 1-(4-Bromo-2-tert-butylphenyl)pyrrolidine

In a manner analogous to example 1 b, the process is carried out by a reaction of 10 g (44 mmol) of 4-bromo-2-tert-butylphenylamine with 3.8 g (96 mmol) of 60% sodium hydride and with 3.4 ml (96 mmol) of 1,4-dibromobutane. 7.6 g of 1-(4-bromo-2-tert-butylphenyl)-pyrrolidine are obtained in the form of an oil (yield=61%).

b/ 3-tert-Butyl-4-pyrrolidin-1-ylbenzaldehyde

In a manner analogous to example 1 d, the process is carried out by a reaction of 7.6 g (27 mmol) of 1-(4-bromo-2-tert-butylphenyl)pyrrolidine with 16.2 ml (40 mmol) of a 2.5M solution of n-butyllithium and 3.1 ml (40 mmol) of DMF. 5 g of 3-tert-butyl-4-pyrrolidin-1-ylbenzaldehyde are obtained in the form of a yellow oil (yield=80%).

c/ 1-(3-tert-Butyl-4-pyrrolidin-1-ylphenyl)prop-2-yn-1-ol

In a manner analogous to example 1 e, the process is carried out by a reaction of 1 g (4 mmol) of 3-tert-butyl-4-pyrrolidin-1-ylbenzaldehyde with 11 ml (5.5 mmol) of a 0.5M solution of ethynylmagnesium bromide. 640 mg of 1-(3-tert-butyl-4-pyrrolidin-1-ylphenyl)prop-2-yn-1-ol are obtained in the form of a colourless oil (yield=62%).

d/ 4-[3-(3-tert-butyl-4-pyrrolidin-1-ylphenyl)-3-hydroxyprop-1-ynyl]benzoic acid In a manner analogous to example 1 e, the process is carried out by a reaction of 640 mg (2.5 mmol) of 1-(3-tert-butyl-4-pyrrolidin-1-ylphenyl)prop-2-yn-1-ol with 520 mg (2.1 mmol) of 4-iodobenzoic acid, 20 mg (0.1 mmol) of copper iodide and 37 mg (0.05 mmol) of bis(triphenylphosphine) palladium chloride. 360 mg of 4-[3-(3-tert-butyl-4-pyrrolidin-1-ylphenyl)-3-hydroxyprop-1-ynyl]benzoic acid are obtained in the form of a beige solid (Mp=150° C., yield=46%).

¹H NMR (CDCl₃, 400 MHz):
1.39 (s, 9H), 1.87 (m, 4H), 2.91 (m, 4H), 4.10 (s, 1H), 5.60 (s, 1H), 7.34 (d, J=8 Hz, 1H), 7.45 (m, 3H), 7.55 (d, J=2 Hz, 1H), 7.94 (s, 1H), 7.96 (s, 1H).

EXAMPLE 5

4-[3-(3-tert-butyl-4-piperidin-1-ylphenyl)-3-hydroxyprop-1-ynyl]benzoic acid a/ 1-(4-Bromo-2-tert-butylphenyl)piperidine

In a manner analogous to example 1 b, the process is carried out by a reaction of 10 g (44 mmol) of 4-bromo-2-tert-butylphenylamine with 3.8 g (96 mmol) of 60% sodium hydride and with 3.4 ml (96 mmol) of 1,4-dibromobutane. 9.9 g of 1-(4-bromo-2-tert-butylphenyl)-piperidine are obtained in the form of an oil (yield=76%).

b/ 3-tert-Butyl-4-piperidin-1-ylbenzaldehyde

In a manner analogous to example 1 d, the process is carried out by a reaction of 9.9 g (34 mmol) of 1-(4-bromo-2-tert-butylphenyl)piperidine with 20 ml (50 mmol) of a 2.5M solution of n-butyllithium and 3.9 ml (50 mmol) of DMF. 8.8 g of 3-tert-butyl-4-piperidin-1-ylbenzaldehyde are obtained in the form of a yellow oil (yield=100%).

c/ 1-(3-tert-Butyl-4-piperidin-1-ylphenyl)prop-2-yn-1-ol

In a manner analogous to example 1 e, the process is carried out by a reaction of 1 g (4 mmol) of 3-tert-butyl-4-piperidin-1-ylbenzaldehyde with 12 ml (6 mmol) of a 0.5M solution of ethynylmagnesium bromide. 890 mg of 1-(3-tert-Butyl-4-piperidin-1-ylphenyl)prop-2-yn-1-ol are obtained in the form of a colourless oil (yield=82%).

d/ 4-[3-(3-tert-Butyl-4-piperidin-1-ylphenyl)-3-hydroxyprop-1-ynyl]benzoic acid In a manner analogous to example 1 e, the process is carried out by a reaction of 1.18 g (4.4 mmol) of 1-(3-tert-butyl-4-piperidin-1-ylphenyl)prop-2-yn-1-ol with 890 mg (3.6 mmol) of 4-iodobenzoic acid, 35 mg (0.18 mmol) of copper iodide and 63 mg (0.09 mmol) of bis(triphenylphosphine) palladium chloride. 650 mg of 4-[3-(3-tert-butyl-4-piperidin-1-ylphenyl)-3-hydroxyprop-1-ynyl]benzoic acid are obtained in the form of a beige solid (Mp=112° C., yield=46%).

¹H NMR (CDCl₃, 400 MHz):
1.41 (s, 9H), 1.57 (m, 4H), 1.65 (m, 1H), 2.68 (m, 5H), 5.57 (d, J=4 Hz, 1H), 6.13 (d, J=8 Hz, 1H), 7.38 (s, 2H), 7.49 (s, 1H), 7.54 (d, J=8 Hz, 2H), 7.92 (d, J=8 Hz, 2H).

EXAMPLE 6

4-[3-(3-tert-butyl-4-diethylaminophenyl)-3-hydroxyprop-1-ynyl]-2-hydroxybenzoic acid a/ Methyl 4-[3-(3-tert-butyl-4-diethylaminophenyl)-3-hydroxyprop-1-ynyl]-2-hydroxybenzoate In a manner analogous to example 1 e, the process is carried out by a reaction of 3.7 g (15 mmol) of 1-(3-tert-butyl-4-diethylaminophenyl)prop-2-yn-1-ol with 3.3 g (12 mmol) of methyl 4-iodosalicylate, 114 mg (0.6 mmol) of copper iodide and 210 mg (0.3 mmol) of bis(triphenylphosphine)palladium chloride. 4 g of methyl 4-[3-(3-tert-butyl-4-diethylaminophenyl)-3-hydroxyprop-1-ynyl]-2-hydroxybenzoate are obtained in the form of yellow oil (yield=66%).

b/ 4-[3-(3-tert-Butyl-4-diethylaminophenyl)-3-hydroxy-prop-1-ynyl]-2-hydroxybenzoic acid 1.7 g (4.3 mmol) of methyl 4-[3-(3-tert-butyl-4-diethylaminophenyl)-3-hydroxyprop-1-ynyl]-2-hydroxybenzoate are dissolved in 50 ml of THF with 1 ml of methanol and 2 ml of 1N aqueous NaCH. The solution is stirred at ambient temperature for 2 hours and then 2 days at reflux. The reaction medium is poured into a saturated solution of ammonium chloride, and the aqueous phase is brought to acidic pH with 1N HCl and then extracted twice with ethyl acetate. The organic phase is dried over magnesium sulphate and then concentrated to dryness. The residue is purified by chromatography (heptane/ethyl acetate: 50/50). 760 mg of 4-[3-(3-tert-butyl-4-diethylaminophenyl)-3-hydroxy-prop-1-ynyl]-2-hydroxybenzoic acid are obtained in the form of a whitish solid (Mp=245° C., yield=45%).

$^1$H NMR (CDCl$_3$, 400 MHz):

1.01 (t, J=8 Hz, 6H), 1.44 (s, 9H), 2.85 (m, 4H), 5.58 (s, 1H), 6.10 (s, 1H), 6.97 (d, J=6.4 Hz, 2H), 7.29 (d, J=8 Hz, 1H), 7.37 (d, J=8 Hz, 1H), 7.55 (s, 1H), 7.77 (d, J=8.4 Hz, 1H).

EXAMPLE 7

4-[3-(3-tert-butyl-5-chloro-4-dimethylamino-phenyl)-3-hydroxyprop-1-ynyl]benzoic acid a/ 4-Bromo-2-tert-butyl-6-chlorophenylamine 6.4 g (48 mmol) of N-chlorosuccinimide are added to a solution of 10 g (44 mmol) of 4-bromo-2-tert-butylphenylamine (example 1a) in 150 ml of DMF. The medium is heated at 70° C. for 2 hours. It is then poured into a saturated aqueous solution of sodium chloride and extracted with ethyl acetate. The organic phases are combined and washed with water and then dried over sodium sulphate. The residue is chromatographed on silica gel (90/10 heptane/ethyl acetate). 11.4 g of 4-bromo-2-tert-butyl-6-chlorophenylamine are obtained in the form of an orange oil (yield=99%).

b/
(4-Bromo-2-tert-butyl-6-chlorophenyl)methylamine

In a manner analogous to example 1 b, the process is carried out by a reaction of 3 g (11.4 mmol) of 4-bromo-2-tert-butyl-6-chlorophenylamine with 1 g (25 mmol) of sodium hydride and 1.6 ml (25.7 mmol) of methyl iodide. 2.54 g of (4-bromo-2-tert-butyl-6-chlorophenyl)methylamine are obtained in the form of an orange oil (yield=80%).

c/
(4-Bromo-2-tert-butyl-6-chlorophenyl)dimethylamine

In a manner analogous to example 1 c, the process is carried out by a reaction of 2.54 g (9.2 mmol) of (4-bromo-2-tert-butyl-6-chlorophenyl)methylamine with 850 mg (21.3 mmol) of sodium hydride and 1.3 ml (21 mmol) of methyl iodide. 2 g of (4-bromo-2-tert-butyl-6-chlorophenyl)dimethylamine are obtained in the form of a yellow oil (yield=75%).

d/
3-tert-Butyl-5-chloro-4-dimethylaminobenzaldehyde

In a manner analogous to example 1 d, the process is carried out by a reaction of 2.25 ml (5.6 mmol) of 2.5M n-butyllithium/hexane with 1.5 g (5.2 mmol) of (4-bromo-2-tert-butyl-6-chlorophenyl)dimethylamine and 450 µl (5.8 mmol) of dimethylformamide. 1.23 g of 3-tert-butyl-5-chloro-4-dimethylaminobenzaldehyde are obtained in the form of a yellow oil (yield=99%).

e/ 1-(3-tert-Butyl-5-chloro-4-dimethylaminophenyl)prop-2-yn-1-ol

In a manner analogous to example 1 e, the process is carried out by a reaction of 13 ml (6.5 mmol) of 0.5M ethynylmagnesium bromide/THF with 1.2 g (5 mmol) of 3-tert-butyl-5-chloro-4-dimethylaminobenzaldehyde. 650 mg of 1-(3-tert-butyl-5-chloro-4-dimethylamino-phenyl)prop-2-yn-1-ol are obtained in the form of a yellow solid (yield=49%).

f/ 4-[3-(3-tert-Butyl-5-chloro-4-dimethylaminophenyl)-3-hydroxyprop-1-ynyl]benzoic acid In a manner analogous to example 1 f, the process is carried out by a reaction of 200 mg (0.8 mmol) of 4-iodobenzoic acid with 300 mg (1.1 mmol) of 1-(3-tert-butyl-5-chloro-4-dimethylaminophenyl)prop-2-yn-1-ol in the presence of 8 mg (0.04 mmol) of copper iodide and 16 mg (0.02 mmol) of bis(triphenylphosphine)palladium chloride. 270 mg of 4-[3-(3-tert-butyl-5-chloro-4-dimethylaminophenyl)-3-hydroxyprop-1-ynyl]benzoic acid are obtained in the form of a whitish solid (Mp=120° C., yield=87%).

$^1$H NMR (CDCl$_3$, 400 MHz):

1.45 (s, 9H); 2.84 (s, 6H); 5.65 (s, 1H); 7.49-7.50 (d, 1H, J=2 Hz); 7.53-7.54 (d, 1H, J=2 Hz); 7.58-7.60 (d, 2H, J=6.85 Hz); 8.08-8.1 (d, 2H, J=6.85 Hz).

EXAMPLE 8

4-[3-(3-tert-butyl-5-chloro-4-dimethylamino-phenyl)-3-hydroxyprop-1-ynyl]-2-hydroxybenzoic acid a/ 4-[3-(3-tert-Butyl-5-chloro-4-dimethylaminophenyl)-3-hydroxyprop-1-ynyl]-2-hydroxybenzoic acid In a manner analogous to example 1 f, the process is carried out by a reaction of 220 mg (0.83 mmol) of 2-hydroxy-4-iodobenzoic acid with 320 mg (1.2 mmol) of 1-(3-tert-butyl-5-chloro-4-dimethylaminophenyl)prop-2-yn-1-ol in the presence of 9 mg (0.05 mmol) of copper iodide and 17 mg (0.025 mmol) of bis(triphenyl-phosphine)palladium chloride. 140 mg of 4-[3-(3-tert-butyl-5-chloro-4-dimethylaminophenyl)-3-hydroxyprop-1-ynyl]-2-hydroxybenzoic acid are obtained in the form of a yellowish oil (Mp=175° C., yield=42%).

$^1$H NMR (CDCl$_3$, 400 MHz):

1.39 (s, 9H); 2.77 (s, 6H); 5.55 (s, 1H); 6.90-6.93 (dd, 1H, J=1.44 Hz, J'=6.72 Hz); 7.0 (d, 1H, J=1.32 Hz); 7.42-7.43 (d, 1H, J=2.08 Hz); 7.47-7.48 (d, 1H, J=2.04 Hz); 7.76-7.78 (d, 1H, J=8.12 Hz).

EXAMPLE 9

4-[3-(4-dimethylamino-3,5-diisopropyl-phenyl)-3-hydroxyprop-1-ynyl]benzoic acid a/ 4-Bromo-2,6-diisopropylphenylamine 40.8 g (85 mmol) of tetra-n-butylammonium tribromide are added, at 0° C. and portionwise, to a solution of 15 g (85 mmol) of 2,6-diisopropylphenyl-amine in 200 ml of tetrahydrofuran. The medium is stirred for 2 h. It is then poured into a saturated aqueous solution of sodium thiosulphate and extracted with ethyl acetate. The organic phases are combined and washed with water. They are dried over sodium sulphate. The residue is purified by silica gel chromatography (80/20 heptane/ethyl acetate). 20.6 g of 4-bromo-2,6-diisopropylphenylamine are obtained in the form of a yellow oil (yield=95%).

b/ (4-Bromo-2,6-diisopropylphenyl)dimethylamine

A solution of 12 g (47 mmol) of 4-bromo-2,6-diisopropylphenylamine in 100 ml of DMSO is added to 4.1 g (100 mmol) of sodium hydride in 20 ml of DMSO. The medium is stirred for 1 h and then 6.4 ml (100 mmol) of methyl iodide are added. The medium is heated at 45° C. for 3 hours and then poured into a saturated aqueous solution of ammonium chloride and extracted with ethyl acetate. The organic phases are combined and washed with water. They are dried over sodium sulphate. The residue is purified by silica gel chromatography (90/10 heptane/ethyl acetate). 8.7 g of (4-bromo-2,6-diisopropylphenyl)dimethylamine are obtained in the form of a white solid (yield=65%).

c/ 4-Dimethylamino-3,5-diisopropylbenzaldehyde

In a manner analogous to example 1 d, the process is carried out by a reaction of 5.5 ml (13.8 mmol) of 2.5M n-butyllithium/hexane with 3.3 g (11.6 mmol) of 4-bromo-2,6-diisopropylphenyl)dimethylamine and 1.1 ml (14 mmol) of dimethylformamide. 2.6 g of 4-dimethylamino-3,5-diisopropylbenzaldehyde are obtained in the form of a yellow oil (yield=96%).

d/ 1-(4-dimethylamino-3,5-diisopropylphenyl)prop-2-yn-1-ol

In a manner analogous to example 1 e, the process is carried out by a reaction of 28 ml (14 mmol) of 0.5M ethynylmagnesium bromide/THF with 1.2 g (5 mmol) of 4-dimethylamino-3,5-diisopropylbenzaldehyde. 2.5 g of 1-(4-dimethylamino-3,5-diisopropylphenyl)prop-2-yn-1-ol are obtained in the form of a whitish solid (yield=90%).

e/ 4-[3-(4-Dimethylamino-3,5-diisopropylphenyl)-3-hydroxyprop-1-ynyl]benzoic acid In a manner analogous to example 1 f, the process is carried out by a reaction of 335 mg (1.35 mmol) of 4-iodobenzoic acid with 500 mg (1.9 mmol) of 1-(4-dimethylamino-3,5-diisopropylphenyl)prop-2-yn-1-ol in the presence of 15 mg (0.08 mmol) of copper iodide and 27 mg (0.04 mmol) of bis(triphenylphosphine)palladium chloride. 190 mg of 4-[3-(3-tert-butyl-5-chloro-4-dimethylaminophenyl)-3-hydroxyprop-1-ynyl]benzoic acid are obtained in the form of a whitish solid (Mp=198° C., yield=37%).
$^1$H NMR (CDCl$_3$, 400 MHz):
1.25 (s, 6H); 1.27 (s, 6H); 2.85 (s, 3H); 2.87 (s, 3H); 3.37-3.41 (c, 2H); 5.68 (s, 1H); 7.34 (s, 2H); 7.58-7.60 (d, 2H, J=8.4 Hz); 8.07-8.1 (d, 2H, J=8.4 Hz).

EXAMPLE 10

4-[3-(4-dimethylamino-3,5-diisopropyl-phenyl)-3-hydroxyprop-1-ynyl]-2-hydroxybenzoic acid a/ 4-[3-(4-Dimethylamino-3,5-diisopropylphenyl)-3-hydroxyprop-1-ynyl]-2-hydroxybenzoic acid In a manner analogous to example 1 f, the process is carried out by a reaction of 360 mg (1.35 mmol) of 2-hydroxy-4-iodobenzoic acid with 500 mg (1.9 mmol) of 1-(4-dimethylamino-3,5-diisopropylphenyl)prop-2-yn-1-ol in the presence of 15 mg (0.08 mmol) of copper iodide and 27 mg (0.04 mmol) of bis(triphenylphosphine)-palladium chloride. 120 mg of 4-[3-(4-dimethylamino-3,5-diisopropylphenyl)-3-hydroxyprop-1-ynyl]-2-hydroxy-benzoic acid are obtained in the form of a yellowish solid (Mp: dec>250° C., yield=22%).
$^1$H NMR (CDCl$_3$, 400 MHz):
1.19 (s, 6H); 1.21 (s, 6H); 2.79 (s, 3H); 2.81 (s, 3H); 3.31-3.34 (c, 2H); 5.59 (s, 1H); 6.91-6.93 (dd, 1H, J=1.44 Hz, J'=6.76 Hz); 7.01 (d, 1H, J=1.24 Hz); 7.28 (s, 2H); 7.77-7.79 (d, 1H, J=8.16 Hz); 11.25 (s, 1H).

EXAMPLE 11

4-[3-(4-diethylamino-3-isopropylphenyl)-3-hydroxyprop-1-ynyl]benzoic acid

1/ 4-Bromo-2-isopropylphenylamine

In a manner analogous to example 9a, the process is carried out by a reaction of 89 g (185 mmol) of tetra-n-butylammonium tribromide with 25 g (185 mmol) of 2-isopropylaniline. 22 g of 4-bromo-2-isopropyl-phenylamine are obtained (yield=57%).

b/ (4-Bromo-2-isopropylphenyl)ethylamine

In a manner analogous to example 9b, the process is carried out by a reaction of 6.9 g (32 mmol) of 4-bromo-2-isopropylphenylamine with 2.8 g (70 mmol) of sodium hydride and 57 ml (71 mmol) of ethyl iodide. 7.4 g of crude (4-bromo-2-isopropylphenyl)ethylamine are obtained.

c/ (4-Bromo-2-isopropylphenyl)diethylamine

In a manner analogous to example 9c, the process is carried out by a reaction of 7.4 g of (4-bromo-2-isopropylphenyl)ethylamine with 2.8 g (70 mmol) of sodium hydride and 5.7 ml (71 mmol) of ethyl iodide. 4.8 g of (4-bromo-2-isopropylphenyl)diethylamine are obtained (yield=56%).

d/ 4-Diethylamino-3-isopropylbenzaldehyde

In a manner analogous to example 1 d, the process is carried out by a reaction of 1.8 ml (4.4 mmol) of 2.5M n-butyllithium/hexane with 1 g (3.7 mmol) of (4-bromo-2-isopropylphenyl)diethylamine and 0.35 ml (4.5 mmol) of dimethylformamide. 790 mg of 4-diethylamino-3-isopropylbenzaldehyde are obtained in the form of a yellow oil (yield=97%).

e/ 1-(4-Diethylamino-3-isopropylphenyl)prop-2-yn-1-ol

In a manner analogous to example 1 e, the process is carried out by a reaction of 9.3 ml (4.7 mmol) of 0.5M ethynylmagnesium bromide/THF with 780 mg (3.5 mmol) of 4-diethylamino-3-isopropylbenzaldehyde. 720 mg of 1-(4-diethylamino-3-isopropylphenyl)prop-2-yn-1-ol are obtained in the form of a yellow oil (yield=83%).

f/ 4-[3-(4-Diethylamino-3-isopropylphenyl)-3-hydroxy-prop-1-ynyl]benzoic acid

In a manner analogous to example 1 f, the process is carried out by a reaction of 248 mg (1 mmol) of 4-iodobenzoic acid with 350 mg (1.4 mmol) of 1-(4-diethylamino-3-isopropylphenyl)prop-2-yn-1-ol in the presence of 11 mg (0.06 mmol) of copper iodide and 20 mg (0.03 mmol) of bis(triphenylphosphine)palladium chloride. 240 mg of 4-[3-(4-diethylamino-3-isopropylphenyl)-3-hydroxyprop-1-ynyl]benzoic acid are obtained in the form of a whitish solid (Mp=145° C., yield=46%).
$^1$H NMR (CDCl$_3$, 400 MHz):

0.99 (s, 3H); 1.01 (s, 3H); 1.21 (s, 3H); 1.23 (s, 3H); 2.98-2.99 (c, 4H): 3.67-3.72 (c, 1H); 5.70 (s, 1H); 7.17-7.19 (d, 1H, J=8.22 Hz); 7.41-7.43 (dd, 1H, J=1.8 Hz, J'=6.26 Hz); 7.52 (d, 1H, J=1.63 Hz); 7.58-7.6 (d, 2H, J=8.22 Hz); 8.07-8.10 (d, 2H, J=8.22 Hz).

EXAMPLE 12

Transactivation Assay

The activation of receptors with an agonist (activator) in HeLa cells leads to the expression of a reporter gene, luciferase, which, in the presence of a substrate, generates light. The activation of the receptors can thus be measured by quantifying the luminescence produced after incubation of the cells in the presence of a reference agonist. Inhibitory products will displace the agonist from its site, thus preventing activation of the receptor. The activity is measured by quantifying the decrease in light produced. This measurement makes it possible to determine the inhibitory activity of the compounds according to the invention.

In this study, a constant is determined which represents the affinity of the molecules for the receptor. Since this value can fluctuate depending on the basal activity and the expression of the receptor, it is referred to as the Kd apparent (KdApp).

To determine this constant, "crossed curves" of the test product against a reference agonist, 4-[2-(5,5,8,8-tetramethyl-5,6,7,8-tetrahydronaphthalen-2-yl)propenyl]benzoic acid, are realized in 96-well plates. The test product is used at 10 concentrations and the reference agonist at 7 concentrations. In each well, the cells are in contact with a concentration of the test product and with a concentration of the reference agonist, 4-[2-(5,5,8,8-tetramethyl-5,6,7,8-tetrahydronaphthalen-2-yl)]propenyl]benzoic acid. Measurements are also carried out for the total agonist control (4-[2-(5,5,8,8-tetramethyl-5,6,7,8-tetrahydro-naphthalen-2-yl)propenyl]benzoic acid) and the inverse agonist control, 4-{(E)-3[4-(4-tert-butylphenyl)-5,5,8,8-tetramethyl-5,6,7,8-tetrahydronaphthalen-2-yl]-3-oxopropenyl}benzoic acid.

These crossed curves make it possible to determine the AC50 values (concentration at which 50% activation is observed) for the reference ligand at various concentrations of test product. These AC50 values are used to calculate the Schild regression by plotting a straight line corresponding to the Schild equation ("*Quantitation in receptor pharmacology*" Tervy P. Kenakin, Receptors and Channels, 2001, 7, 371-385).

The HeLa cell lines used are stable transfectants containing the ERE-βGlob-Luc-SV-Neo (reporter gene) and RAR (α, β, γ) ER-DBD-puro plasmids. These cells are seeded in 96-well plates at a rate of 10 000 cells per well in 100 µl of DMEM medium without phenol red, supplemented with 10% of defatted calf serum. The plates are then incubated at 37° C., 7% $CO_2$, for 4 hours.

The various dilutions of the test products, of the reference ligand (4-[2-(5,5,5,8-tetramethyl-5,6,7,8-tetrahydronaphthalen-2-yl)propenyl]benzoic acid), of the 100% control (100 nM 4-[2-(5,5,8,8-tetramethyl-5,6,7,8-tetrahydronaphthalen-2-yl)propenyl]benzoic acid) and of the 0% control (500 nM 4-{(E)-3-[4-(4-tert-butylphenyl)-5,5,8,8-tetramethyl-5,6,7,8-tetrahydronaphthalen-2-yl]-3-oxopropenyl}benzoic acid) are added in a proportion of 5 µl per well. The plates are then incubated for 18 hours at 37° C., 7% $CO_2$. The culture medium is removed by turning the plates over, and 100 µl of a 1:1 PBS/luciferin mixture are added to each well. After 5 minutes, the plates are read using a luminescence reader.

|  | RARα Kdapp (nM) | RARβ Kdapp (nM) | RARγ Kdapp (nM) |
|---|---|---|---|
| Compound of example 1 | 625 | 185 | 37.5 |
| Compound of example 2 | 3000 | 600 | 120 |
| Compound of example 3 | 250 | 120 | 15 |
| Compound of example 4 | 1002 | 252 | 30 |
| Compound of example 5 | 4015 | 2015 | 120 |
| Compound of example 6 | 250 | 500 | 60 |
| Compound of example 7 | 120 | 15 | 2 |
| Compound of example 8 | 250 | 60 | 4 |
| Compound of example 9 | 60 | 60 | 0.5 |
| Compound of example 10 | 1000 | 120 | 1 |
| Compound of example 11 | 1000 | 60 | 30 |

The results obtained with the compounds of the invention clearly show Kdapp values of less than or equal to 1000 nM.

EXAMPLE 13

Formulation Examples

In this example, various concrete formulations based on the compounds according to the invention have been illustrated.

| A/ Oral administration | |
|---|---|
| (a) 0.2 g tablet | |
| Compound of example 5 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Oral suspension in 5 ml vials | |
| Compound of example 3 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavouring | qs |
| Purified water | qs 5 ml |
| (c) 0.8 g tablet | |
| Compound of example 2 | 0.500 g |
| Pregelatinized starch | 0.100 g |
| Microcrystalline cellulose | 0.115 g |
| Lactose | 0.075 g |
| Magnesium stearate | 0.010 g |
| (d) Oral suspension in 10 ml vials | |
| Compound of example 2 | 0.200 g |
| Glycerol | 1.000 g |
| 70% sorbital | 1.000 g |
| Sodium saccharinate | 0.010 g |
| Methyl para-hydroxybenzoate | 0.080 g |
| Flavouring | qs |
| Purified water | qs 10 ml |
| B/ Parenteral administration | |
| (a) Composition | |
| Compound of example 3 | 0.002 g |
| Ethyl oleate | qs 10 g |
| (b) Composition | |
| Compound of example 1 | 0.05% |
| Polyethylene glycol | 20% |
| 0.9% NaCl solution | qs 100 |

-continued

| (c) Composition | |
|---|---|
| Compound of example 3 | 2.5% |
| Polethylene glycol 400 | 20% |
| 0.9% NaCl solution | qs 100 |
| (d) Injectable cyclodextrin composition | |
| Compound of example 3 | 0.1 mg |
| β-cyclodextrin | 0.10 g |
| Water for injection | qs 10.00 g |

C/ Topical administration

| (a) Ointment | |
|---|---|
| Compound of example 2 | 0.020 g |
| Isopropyl myristate | 81.700 g |
| Liquid petroleum jelly fluid | 9.100 g |
| Silica ("Aerosil 200" sold by Degussa) | 9.180 g |
| (b) Ointment | |
| Compound of example 5 | 0.300 g |
| White petroleum jelly codex | qs 100 g |
| (c) Non-ionic water-in-oil cream | |
| Compound of example 2 | 0.100 g |
| Mixture of emulsifying lanolin alcohols, waxes and oils ("Anhydrous eucerin" sold by BDF) | 39.900 g |
| Methyl para-hydroxybenzoate | 0.075 g |
| Propyl para-hydroxybenzoate | 0.075 g |
| Sterile demineralized water | qs 100 g |
| (d) Lotion | |
| Compound of example 2 | 0.100 g |
| Polyethylene glycol (PEG 400) | 69.900 g |
| 95% ethanol | 30.00 g |
| (e) Hydrophobic ointment | |
| Compound of example 2 | 0.300 g |
| Isopropyl myristate | 36.400 g |
| Silicone oil ("Rhodorsil 47 V 300") sold by Rhone-Poulenc) | 36.400 g |
| Beeswax | 13.600 g |
| Silicone oil ("Ail 300.00 cst" sold by Goldschmidt) | qs 100 g |
| (f) Non-ionic oil-in-water cream | |
| Compound of example 5 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

I claim:

1. At least one chemical entity chosen from compounds, salts, and optical isomers of formula (I):

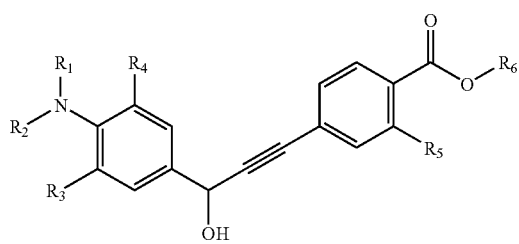

in which:
R₁ is chosen from hydrogen, alkyl radicals containing from 1 to 4 carbon atoms and R₂ is an alkyl radical containing from 1 to 4 carbon atoms, or, alternatively, R₁ and R₂ form, together with the nitrogen atom N to which they are attached, a heterocycle of piperidine or pyrrolidine type,
R₃ is an alkyl radical containing from 1 to 4 carbon atoms,
R₄ is chosen from hydrogen, alkyl radicals containing from 1 to 4 carbon atoms, and halogens,
R₅ is chosen from hydrogen and a hydroxyl radical, and
R₆ is chosen from hydrogen and alkyl radicals containing from 1 to 4 carbon atoms.

2. The at least one chemical entity according to claim 1, wherein the at least one chemical entity chosen from compounds, salts, and optical isomers of formula (I) has at least one of the following characteristics:
R₁ is chosen from a hydrogen atom or a methyl or ethyl radical and R₂ is chosen from methyl, ethyl and a 2-methylpropyl radicals,
R₁ and R₂ form, together with the nitrogen atom N to which they are attached, a heterocycle of piperidine or pyrrolidine type,
R₃ is chosen from i-propyl and t-butyl radicals, and
R₄ is chosen from hydrogen, chlorine, and , methyl, ethyl, and i-propyl radicals.

3. The at least one chemical entity according to claim 2, wherein the at least one chemical entity chosen from compounds, salts, and optical isomers of formula (I) has the following characteristics:
R₁ is chosen from hydrogen and methyl and ethyl radicals and R₂ is chosen from methyl, ethyl, and 2-methylpropyl radicals, or, alternatively, R₁ and R₂ form, together with the nitrogen atom N to which they are attached, a heterocycle of piperidine or pyrrolidine type,
R₃ is chosen from i-propyl and t-butyl radicals, and
R₄ is chosen from hydrogen, chlorine, and methyl, ethyl, and i-propyl radicals.

4. The at least one chemical entity according to claim 1, wherein the at least one chemical entity chosen from compounds, salts, and optical isomers of formula (I) is chosen from alkali metal salts, alkaline-earth metal salts, zinc salts, and organic amine salts thereof.

5. The at least one chemical entity according to claim 1, wherein R₁ is a hydrogen atom or an alkyl radical containing from 1 to 4 carbon atoms, R₂ is an alkyl radical containing from 1 to 4 carbon atoms, and the at least one chemical entity chosen from compounds, salts, and optical isomers of formula (I) is chosen from inorganic acid salts and organic acid salts thereof.

6. At least one chemical entity chosen from:
4-[(tert-butyldiethylaminophenyl)hydroxyprop-1-ynyl]benzoic acid,
4-{[tert-butyl(ethylisobutylamino)phenyl]hydroxyprop-1-ynyl}benzoic acid,
4-[3-(3-tert-butyl-4-dimethylaminophenyl)-3-hydroxyprop-1-ynyl]benzoic acid,
4-[3-(3-tert-butyl-4-pyrrolidin-1-ylphenyl)-3-hydroxyprop-1-ynyl]benzoic acid,
4-[3-(3-tert-butyl-4-piperidin-1-ylphenyl)-3-hydroxyprop-1-ynyl]benzoic acid,
4-[3-(3-tert-butyl-4-diethylaminophenyl)-3-hydroxyprop-1-ynyl]-2-hydroxybenzoic acid,
4-[3-(3-tert-butyl-5-chloro-4-dimethylaminophenyl)-3-hydroxyprop-1-ynyl]benzoic acid,
4-[3-(3-tert-butyl-5-chloro-4-dimethylaminophenyl)-3-hydroxyprop-1-ynyl]-2-hydroxybenzoic acid,
4-[3-(4-dimethylamino-3,5-diisopropylphenyl)-3-hydroxyprop-1-ynyl]benzoic acid, 4-[3-(4-dimethylamino-3,5-diisopropylphenyl)-3-hydroxyprop-1-ynyl]-2-hydroxybenzoic acid, 4-[3-(4-diethylamino-3-isopropylphenyl)-3-hydroxyprop-1-ynyl]benzoic acid, 4-[3-(3-tert-butyl-4-diethylaminophenyl)-3-hydroxyprop-1-ynyl]benzoic acid, and salts and optical isomers thereof.

7. The at least one chemical entity according to claim 6, wherein the at least one chemical entity according to claim 6 is chosen from 4-[(tert-butyldiethylaminophenyl) hydroxyprop-1-ynyl]benzoic acid and salts and optical isomers thereof.

8. The at least one chemical entity according to claim 6, wherein the at least one chemical entity according to claim 6 is chosen from 4-{[tert-butyl (ethylisobutylamino)phenyl]-hydroxyprop-1-ynyl}benzoic acid and salts and optical isomers thereof.

9. The at least one chemical entity according to claim 6, wherein the at least one chemical entity according to claim 6 is chosen from 4-[3-(3-tert-butyl-4-dimethylaminophenyl)-3-hydroxyprop-1-ynyl]benzoic acid and salts and optical isomers thereof.

10. The at least one chemical entity according to claim 6, wherein the at least one chemical entity according to claim 6 is chosen from 4-[3-(3-tert-butyl-4-piperidin-1-ylphenyl)-3-hydroxyprop-1-ynyl]benzoic acid and salts and optical isomers thereof.

11. A medicament comprising the at least one chemical entity claim 1.

12. A pharmaceutical composition comprising, in a physiologically acceptable medium, the at least one chemical entity of claim 1.

13. The composition according to claim 12, wherein the concentration of the at least one chemical entity of claim 1 ranges from 0.001% to 10% by weight, relative to the weight of the composition.

14. The composition according to claim 13, wherein the concentration of the at least one chemical entity of claim 1 ranges from 0.01% to 1% by weight, relative to the weight of the composition.

15. A cosmetic composition comprising, in a cosmetically acceptable medium, the at least one chemical entity of claim 1.

16. The composition according to claim 15, wherein the concentration of the at least one chemical entity ranges from 0.001% to 3% by weight, relative to the total weight of the composition.

* * * * *

UNITED STATES PATENT AND TRADEMARK OFFICE
CERTIFICATE OF CORRECTION

PATENT NO. : 8,163,952 B2
APPLICATION NO. : 12/599624
DATED : April 24, 2012
INVENTOR(S) : Thibaud Biadatti-Portal Page 1 of 1

It is certified that error appears in the above-identified patent and that said Letters Patent is hereby corrected as shown below:

On the Title Page, Item (30), in the "Foreign Application Priority Data",
"07 55019" should read --0755019--.

In claim 2, column 20, lines 17-18, "and a 2-methylpropyl radicals," should read
--and 2-methylpropyl radicals,--.

In claim 2, column 20, line 23, "chlorine, and , methyl," should read
--chlorine, and methyl,--.

In claim 7, column 21, lines 10-11,
"4-[(tert-butyldiethylaminophenyl) hydroxyprop-1-ynyl]benzoic"
should read
--4-[(tert-butyldiethylaminophenyl)hydroxyprop-1-ynyl]benzoic--.

In claim 8, column 21, lines 15-16,
"4-{[tert-butyl (ethylisobutylamino)phenyl]-hydroxyprop-1-ynyl}
benzoic"
should read
--4-{[tert-butyl(ethylisobutylamino)phenyl]-hydroxyprop-1-ynyl}
benzoic--.

In claim 11, column 22, line 5, "entity claim 1." should read --entity of claim 1.--.

Signed and Sealed this
Thirty-first Day of July, 2012

David J. Kappos
*Director of the United States Patent and Trademark Office*